United States Patent [19]

Marsoner et al.

[11] Patent Number: 4,496,512
[45] Date of Patent: Jan. 29, 1985

[54] METHOD FOR MAKING AN ION-SENSITIVE CAPILLARY ELECTRODE

[75] Inventors: Hermann Marsoner; Christoph Ritter, both of Graz, Austria

[73] Assignee: AVL AG, Schaffhausen, Switzerland

[21] Appl. No.: 447,997

[22] Filed: Dec. 8, 1982

Related U.S. Application Data

[62] Division of Ser. No. 000,723, Jan. 3, 1979, abandoned.

[30] Foreign Application Priority Data

Jan. 3, 1978 [CH] Switzerland .......................... 47/788
Jun. 9, 1978 [AT] Austria ................................ 4200/78

[51] Int. Cl.³ ...................... B29C 13/00; B29D 31/00; B29G 7/00
[52] U.S. Cl. ................................... 264/267; 264/334; 264/343
[58] Field of Search ................ 264/138, 262, 263, 267, 264/291, 343, 269, 288.4, 299, 232, 233, 313, 340, 334; 204/296, 411, 412, 418

[56] References Cited

U.S. PATENT DOCUMENTS

| 1,290,205 | 1/1919 | Howell | 285/297 |
|---|---|---|---|
| 2,272,704 | 2/1942 | Harding | 264/314 |
| 2,510,262 | 6/1950 | Sollner et al. | 204/218 |
| 3,556,950 | 1/1971 | Dahms | 264/195 |
| 3,577,332 | 5/1971 | Porter et al. | 204/415 |
| 3,714,015 | 1/1973 | Niedrach | 204/415 |
| 3,875,037 | 4/1975 | Krull | 204/415 |
| 4,056,939 | 11/1977 | Alvarez-Calderon | 249/65 |
| 4,059,406 | 11/1977 | Fleet | 204/412 |
| 4,160,714 | 7/1979 | Anderson et al. | 264/195 |

FOREIGN PATENT DOCUMENTS 2021318 1/1971 Fed. Rep. of Germany .
1047138 11/1966 United Kingdom .

OTHER PUBLICATIONS

Osswald et al., "Flow-Through System . . . ", Chimia, 31, #2, (Feb. 1977), 3 pp.

Primary Examiner—Willard E. Hoag
Attorney, Agent, or Firm—Ladas & Parry

[57] ABSTRACT

Method for making an electrode having an axial capillary bore with an intersecting bore. An extensible tube is inserted in the axial bore and a polymerizable mixture is inserted in the intersecting bore and permitted to polymerize against the tube which is stretched to facilitate removal of the tube. The tube is selected to swell under the action of the solvent and the tube is filled with solvent.

5 Claims, 5 Drawing Figures

METHOD FOR MAKING AN ION-SENSITIVE CAPILLARY ELECTRODE

This is a division of application Ser. No. 000,723 filed Jan. 3, 1979, now abandoned.

BACKGROUND OF THE INVENTION

The present invention relates to a new and improved construction of an ion-sensitive capillary electrode containing an electrode housing in which there is formed a bore and in which there is located a membrane electrode, and further, the invention relates to a new and improved method for the fabrication of such ion-sensitive capillary electrode.

There are known to the art specific ion-selective electrodes for a large number of single or multi-valent ions. They are classified in accordance with the physical condition of the substance which forms the electrode membrane. Consequently, there are known two large groups of ion-selective electrodes:

(1) Ion-selective electrodes having a solid membrane or diaphragm. Such type electrodes can possess either a homogeneous membrane (single crystal, crystalline substance or glass) or an heterogeneous membrane, where a crystalline substance in incorporated in a matrix formed for instance of a polymer.

(2) Ion-selective electrodes with liquid membranes.

In this case the membrane of the electrodes consists of a liquid which is immiscible with water, in which there is dissolved a substance which together with the ion in the solution, for which the electrode is selective, forms an associate or can exchange such.

Such type electrode generally consists of a cylindrical shaft formed of polymeric material at the tip of which there is secured a membrane of the above-mentioned type. The hollow cylindrical shaft contains auxiliary means for producing an electrical contact between the side of the membrane which confronts the interior of the shaft and an electrical leak or shunt conductance. A frequently employed embodiment of such type contact arrangement resides in that an electrolytic solution of suitable composition establishes both the contact with the membrane and also with a conductance electrode (as a rule of the type silver-silver chloride). The conductance electrode can be connected by means of a connection cable with the input of a high ohm amplifier at which there is also connected a standard reference electrode. For measurement purposes the specific ion-sensitive electrode and the reference electrode conjointly immerse in the solution to be examined. The electrical potential difference between the selective ion-sensitive electrode and the reference electrode is a measure for the activity of the ions in the solution and which are to be measured. An embodiment of such type shaft-like specific ion-sensitive electrode has been disclosed for instance in the German Patent Publication No. 2,021,318.

Such type shaft-like selective ion-sensitive electrodes are completely suitable for a large number of fields of application. For the analysis of microsamples having a volume of a few microliters such type electrode however cannot usually be employed, since miniaturization thereof is associated with technological difficulties. Therefore, there have been proposed to the art selective ion-sensitive electrodes wherein the active membrane is present in the form of a capillary or as part of a capillary. Capillary-shaped electrodes, wherein part of the capillary is formed by a liquid membrane, have been disclosed by H. F. Osswald in the publication Chemia, Volume 31, 1977, Nr. 2. It has been found that such type capillary-shaped electrodes exhibit large advantages from the measurement standpoint.

The heretofore known constructional embodiments are however associated with the drawback that a number of electrodes must be mutually connected in a row either by hose sections or prefabricated plastic fitting elements. As a result the exchangeability of the electrodes and the cleaning and drying of the capillaries, following a measurement operation, is rendered more difficult.

SUMMARY OF THE INVENTION

Therefore, with the foregoing in mind it is a primary object of the present invention to provide a new and improved construction of ion-sensitive capillary electrode, and a method of manufacturing the same so as to extensively avoid the aforementioned drawbacks and limitations of the prior art proposals.

Another and more specific object of the present invention aims at avoiding the aforementioned drawbacks of the heretofore known capillary electrodes and providing a capillary-shaped electrode whose number of electrodes can be arranged directly in a row adjacent one another without the need for coupling such electrodes with one another by special hose sections or connection elements.

In keeping with the immediately preceding objective it is a further object of the invention to provide an improved construction of ion-sensitive capillary electrode wherein the individual electrodes nonetheless remain easily exchangeable and are centered in axial direction such that a number of electrode capillaries arranged in a row have a common axis.

A further object of the present invention is to enable also solid body membrane electrodes to be constructed in this fashion with homogeneous or heterogeneous membranes.

Now in order to implement these and still further objects of the invention, which will become more readily apparent as the description proceeds, the invention contemplates that one end of the bore, which is of capillary configuration, is structured for receiving a sealing element. The other end of this bore is constructed in such a manner that it serves as a counter element for the sealing element and thus a number of such type housings can be arranged tightly in a row next to one another.

The method of producing the ion-sensitive capillary electrode contemplates introducing an elastic hose in the axial bore, wherein the diameter of the hose is slightly less than the diameter of the capillary-shaped bore, whereby the intersection location of both bores is sealed. There is introduced into the bore which intersects the axial bore a measured quantity of a polymer mixture in a liquid state and following polymerization or setting thereof the elastic hose is drawn apart so that it tapers or narrows and thus can be removed from the electrode housing.

BRIEF DESCRIPTION OF THE DRAWINGS

The invention will be better understood and objects other than those set forth above, will become apparent when consideration is given to the following detailed description thereof. Such description makes reference to the annexed drawings wherein.

DETAILED DESCRIPTION OF THE PREFERRED EMBODIMENTS

Figure 1:
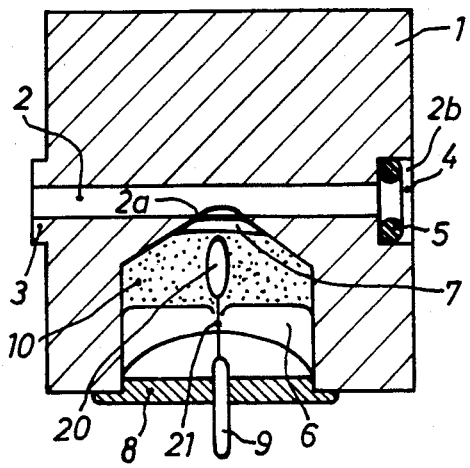
FIG. 1 is a sectional view of a capillary electrode according to the invention containing a liquid membrane.
Figure 2:
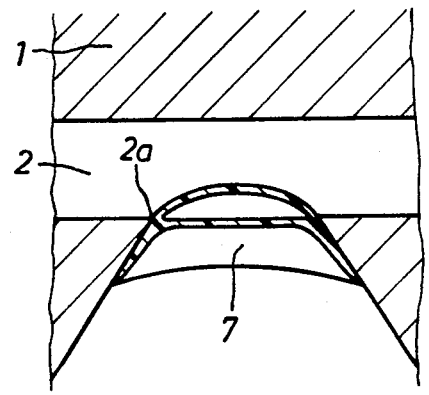
FIG. 2 is a sectional view showing a detail of the capillary electrode of FIG. 1.

Describing now the drawings, wherein throughout the various Figures there have been generally used the same reference characters for the same or analogous components, the liquid membrane electrode shown by way of example in FIG. 1 will be seen to comprise a continuous capillary-shaped axial bore 2 provided in an electrode body or housing 1. Furthermore, extending at preferably right angles to the axial bore 2 is a further bore 6 which conically tapers and intersects the capillary bore 2 at a predetermined intersection location. The opening 2a which is thus formed in the capillary-shaped bore 2 is lined with a thin layer 7 formed of a suitable polymer material which contains a measuring sensitive substance in the form of a liquid ligand (neutral carrier) or an ion exchanger. Contained within the bore 6 is a certain quantity of an electrolyte solution 10 which can be caused to solidify by adding a gelling substance. In this electrolyte solution 10 there immerses a conductance electrode 20, preferably of the type Ag/AgCl which is rigidly connected by means of a conductance wire 21 with a contact pin 9. This contact pin 9 is fixedly mounted in a cover 8 which closes the bore 6.

At a widened end portion 2b of the bore 2 there is inserted a sealing element 5, for example an O-ring. The inner diameter of the sealing O-ring 5 essentially corresponds to the diameter of the capillary bore 2 and the depth of the widened bore portion 2b is greater than the thickness of the sealing element 5. The opposite end of the bore 2, remote from the widened portion 2b defining a recess 4, is provided with a substantially cylindrical plug or protuberance 3. Therefore it is possible to easily interconnect a number of such electrodes arranged in a row with one another by inserting the plug 3 of one electrode into the neighboring recess 4 of the next electrode.

The fabrication of each such type electrode proceeds in the manner that an exactly fitting mandril is introduced into the axial bore 2 and there is introduced into the bore 6 a measured quantity of the liquid electrode membrane substance. Upon evaporation of the solvent contained in the liquid electrode membrane substance the latter polymerizes and forms a thin coating at the open location of the capillary defined by the bore 2. Upon application of this known coating air bubbles remain adhering to the opening 2a of the capillary-shaped bore 2, so that inhomogenities can arise at the membrane. Furthermore, following completion of the polmerization of the membrane, the mandril 2 must be removed by axially shifting the mandril in the bore 2, thereby causing a certain tensile load at the membrane which snugly bears against the mandril, so that damage to the fabricated membrane can arise.

Now with the inventive method for fabricating such type liquid membrane electrode this drawback is avoided in that an elastic hose is introduced into the bore 2. The diameter of this hose, in its relieved state, is slightly larger in size than the internal diameter of the bore 2, so that the elastic hose sealingly bears against the inner wall of the capillary-shaped bore 2. Following application of the membrane liquid at the location 7 the elastic hose can be elongated or extended in axial direction in order to remove possibly arising air bubbles, so that its outer diameter reduces and a small quantity of the membrane liquid can flow directly into the bore. Consequently, air bubbles in the membrane can be eliminated. The thin layer of liquid membrane, which remains in the capillary after relieving the hose and partially lines the inside thereof, is in no way disturbing.

It has been found that the solvent which is contained in the liquid membrane, and which can be caused to vaporize during fabrication, also evaporates into the elastic hose. This leads to detachment of the liquid membrane 7 from the elastic hose and to inhomogenities in the electrode membrane. To avoid this drawback in the fabrication technique it is possible to proceed in a manner such that initially the polymer hose is filled with the same solvent which the liquid membrane 7 also contains. Secondly, the material of the hose is chosen such that this material can be caused to swell by virtue of the solvent. Due to the swelling operation the polymer hose then bears lightly but sealingly at the wall of the bore 2 if its external diameter is slightly less than the internal diameter of the bore 2. By filling the hose with the solvent there is insured that the hose wall possesses the saturation vapor pressure of the solvent, so that the evaporation occurs exclusively in the direction of the bore 6. It has been found that in this way it is possible to fabricate completely homogenous liquid membranes.

Figure 3:
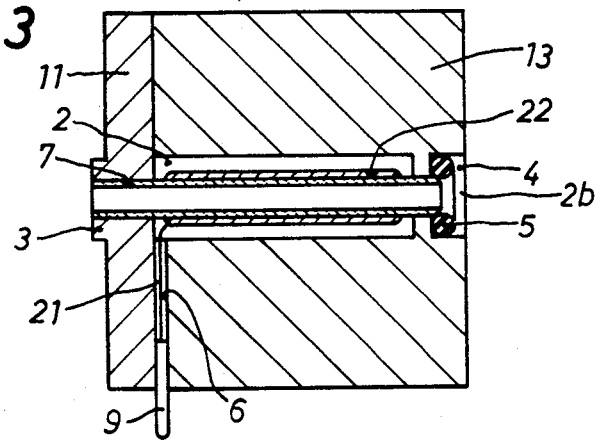
FIG. 3 illustrates the inventive electrode with a glass capillary mounted therein and serving as the measurement sensitive-electrode element.

According to another exemplary embodiment of the inventive capillary electrode it is possible, according to the showing of FIG. 3, to employ such in an arrangement containing a measuring sensitive capillary-shaped glass electrode. To this end the electrode body or housing 1 is divided into two parts 11 and 13. At a region of the electrode housing part 13 the axial bore 2 is enlarged to form the widened portion 2b forming a plug-receiving recess 4 capable of receiving the plug 3 of the next electrode arranged in a row, as previously explained. At the widened end of the electrode body or housing 1 which carries a sealing element 5 as well as at the region of the electrode body or housing part 13 there is sealingly mounted the measuring sensitive glass capillary with an appropriate sealing agent or compound. In the hollow space of the widened axial bore 2 there can be incorporated a conductance or conductor system for the electrode. Such can either be a solid body conductance system, such as for instance silver chloride 22 which is molten onto the glass capillary, the silver chloride 22 being connected by means of a conductance wire 21 extending in the bore 6 with the contact pin 9, or the hollow space or bore 2 can be filled with a likewise gelled electrolyte solution in which there preferably immerses a conductance electrode of the type Ag/AgCl.

Figure 4:
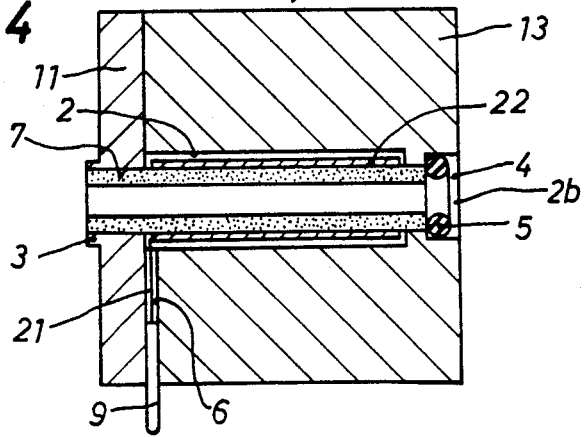
FIG. 4 illustrates a capillary with a solid body electrode incorporated therein.

In completely analogous construction it is possible, according to the showing of FIG. 4, to employ in place of the capillary-shaped, measuring sensitive glass electrode also a capillary-shaped measuring sensitive solid body electrode of a different type. Such type capillary electrode element consist of, for instance, single crystals of lanthanum-fluoride for the fabrication of fluoride-sensitive electrodes or from pressed microcrystalline silver chloride for the fabrication of chloride-sensitive electrodes. Also there are known for these examples in publications a large number of solid body mixtures which can be employed for the specific determination of ions in solutions.

Figure 5:
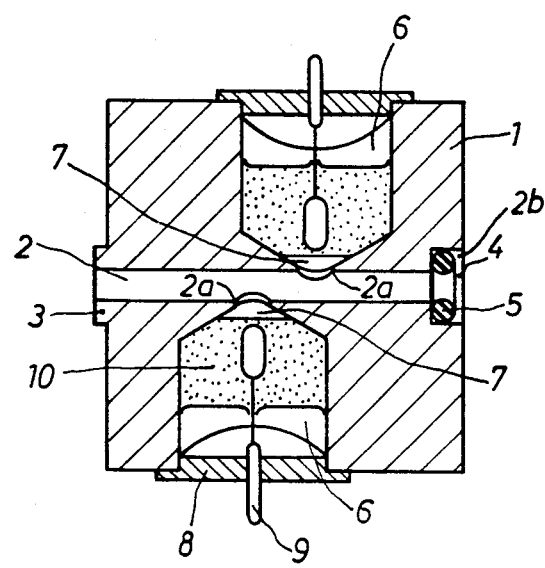
FIG. 5 illustrates the capillary electrode according to the invention having two perpendicular bores.

According to FIG. 5 the electrode body 1 comprises further bores 6 being perpendicular to the capillary-shaped bore 2. Said bores 6 are parallel to each other and they are devided in the radial direction around the capillay-shaped bore 2, i.e. shifted to each other. One end portion of the capillary-shaped bore 2 is provided with a widened portion 26 too in which a sealing element 5 is placed. The openings 2a of said bores 6 are provided with membranes 7. If required, a number of said bores 6 can be carried out in said electrode body 1.

While there are shown and described present preferred embodiments of the invention, it is to be distinctly understood that the invention is not limited thereto, but may be otherwise variously embodied and practiced within the scope of the following claims. Accordingly,

What is claimed is:

1. A method of manufacturing an ion-sensitive capillary electrode containing an electrode housing, the housing having an axial bore there along and a further bore intersecting said axial bore, comprising the steps of:

introducing an elastic hose into said axial bore; sealing an intersection location of the axial bore and the further bore by tightly applying the hose against the wall of the axial bore;

introducing a measured quantity of a polymerizable mixture in a liquid state into the further bore; said mixture being such that the polymerized mixture is releasable from said hose;

polymerizing said mixture and after polymerization thereof extending the elastic hose so that it constricts; and thereafter removing the hose from the electrode housing.

2. The method of claim 1 further comprising the steps of:

filling the elastic hose with a solvent which is the same as that contained in the polymer mixture and which will cause the hose to swell;

permitting the solvent to vaporize and the polymer mixture to polymerize to form a measuring sensitive membrane; and allowing the elastic hose to swell under the action of the solvent;

the diameter of the elastic hose being selected so that after swelling the elastic hose bears tightly against the inner surface of the capillary bore.

3. The method as defined in claim 2, further including the steps of:

utilizing as the polymer mixture a polymer mixture in a liquid form composed of a mixture of a polymer and a solvent, a plasticizer and an active component in the form of an ion exchanger or a ligand which is specific for a certain ion.

4. The method of claim 1, further comprising the step of:

selecting the diameter of the elastic hose to have a diameter slightly larger than that of the capillary shaped bore.

5. The method as defined in claim 4, further including the steps of:

utilizing as the polymeric mixture a polymer mixture in liquid form composed of a mixture of a polymer and a solvent, a plasticizer and an an active component in the form of an ion exchanger or a ligand which is specific for a certain ion.

* * * * *